(12) United States Patent
Nakagawa

(10) Patent No.: US 12,122,802 B2
(45) Date of Patent: Oct. 22, 2024

(54) D-ALLOSE CRYSTAL AND PRODUCTION METHOD THEREOF

(71) Applicant: MATSUTANI CHEMICAL INDUSTRY CO., LTD., Itami (JP)

(72) Inventor: Ryosuke Nakagawa, Osaka (JP)

(73) Assignee: MATSUTANI CHEMICAL INDUSTRY CO., LTD., Itami (JP)

( * ) Notice: Subject to any disclaimer, the term of this patent is extended or adjusted under 35 U.S.C. 154(b) by 0 days.

(21) Appl. No.: 18/138,510

(22) Filed: Apr. 24, 2023

(65) Prior Publication Data

US 2023/0295208 A1    Sep. 21, 2023

Related U.S. Application Data

(62) Division of application No. 17/116,039, filed on Dec. 9, 2020, now Pat. No. 11,673,906.

(30) Foreign Application Priority Data

Dec. 10, 2019    (JP) .................................. 2019-222673

(51) Int. Cl.
*C07H 3/02*    (2006.01)

(52) U.S. Cl.
CPC ............ *C07H 3/02* (2013.01); *C07B 2200/13* (2013.01)

(58) Field of Classification Search
None
See application file for complete search history.

(56) References Cited

U.S. PATENT DOCUMENTS 5,433,793 A * 7/1995 Herber ..................... C07H 3/02
                                                    536/127

FOREIGN PATENT DOCUMENTS

| JP | 2004-298106 A | 10/2004 |
| JP | 2011-205913 A | 10/2011 |
| KR | 10-2019-0134291 A | 12/2019 |

OTHER PUBLICATIONS

Kozakai et al., Bull. Chem. Soc. Jpn., 2015, vol. 88, pp. 465-470. (Year: 2015).*
Taro Kozakai et al., "Aqueous Phase Behavior of the Rare Monosaccharide D-Allose and X-ray Crystallographic Analysis of D-Allose Dihydrate" and its supporting information, Bull. Chem. Soc. Jpn., 2014, 13 pages, vol. 88, No. 3.
Japan Patent Office, Japanese Office Action of JP2019-222673.
European Patent Office Communication issued May 18, 2021 in European application No. 20212642.1.

* cited by examiner

*Primary Examiner* — Traviss C Mcintosh, III
(74) *Attorney, Agent, or Firm* — Sughrue Mion, PLLC

(57) ABSTRACT

High-purity hydrous D-allose crystals and a method of efficiently obtaining the crystals are provided. To a D-allose-containing solution having a purity of D-allose of at least 80% (g/g) in a solute, in a metastable region in a supersaturated state of 30° C. or less, D-allose seed crystals are added. Then, the temperature of the solution is lowered by 10° C. or more for cooling and crystallization to initially obtain "hydrous D-allose crystals", and the crystallization water thereof is removed in a specified temperature zone to obtain novel "anhydrous D-allose crystals".

5 Claims, 3 Drawing Sheets

[FIG. 1]
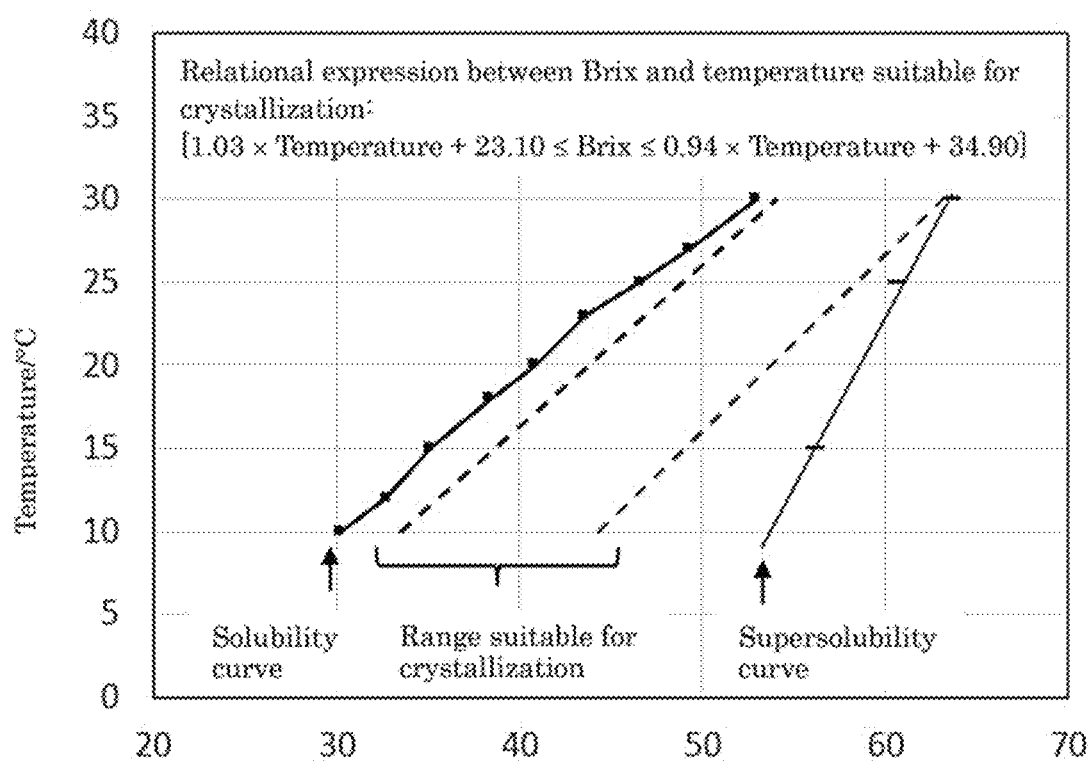

[FIG. 2]
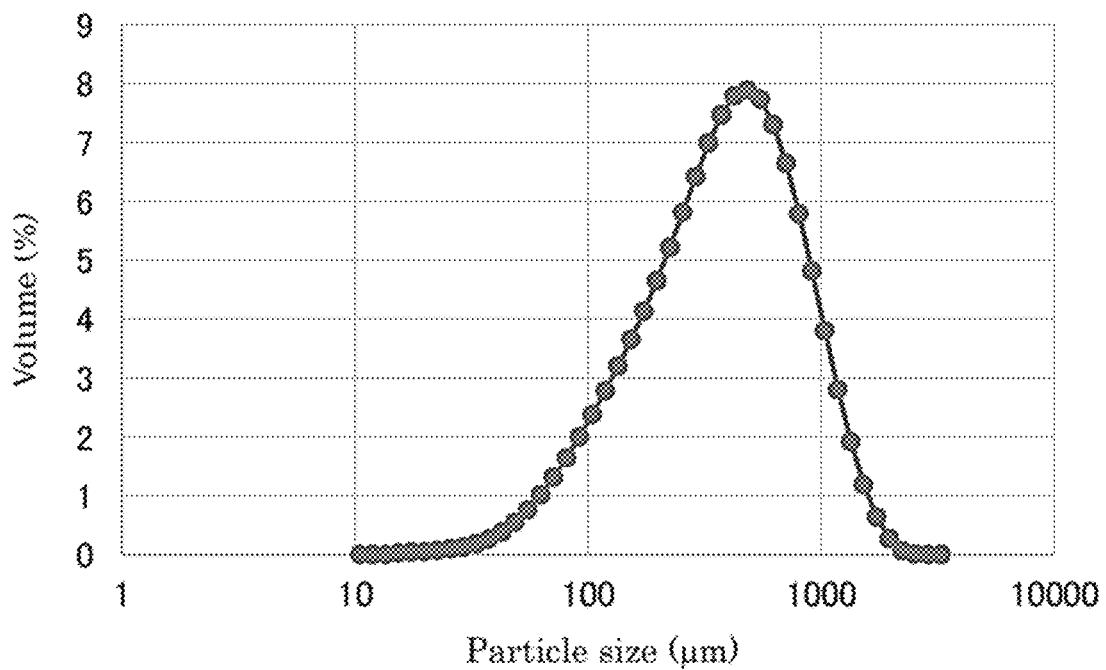

[FIG. 3]
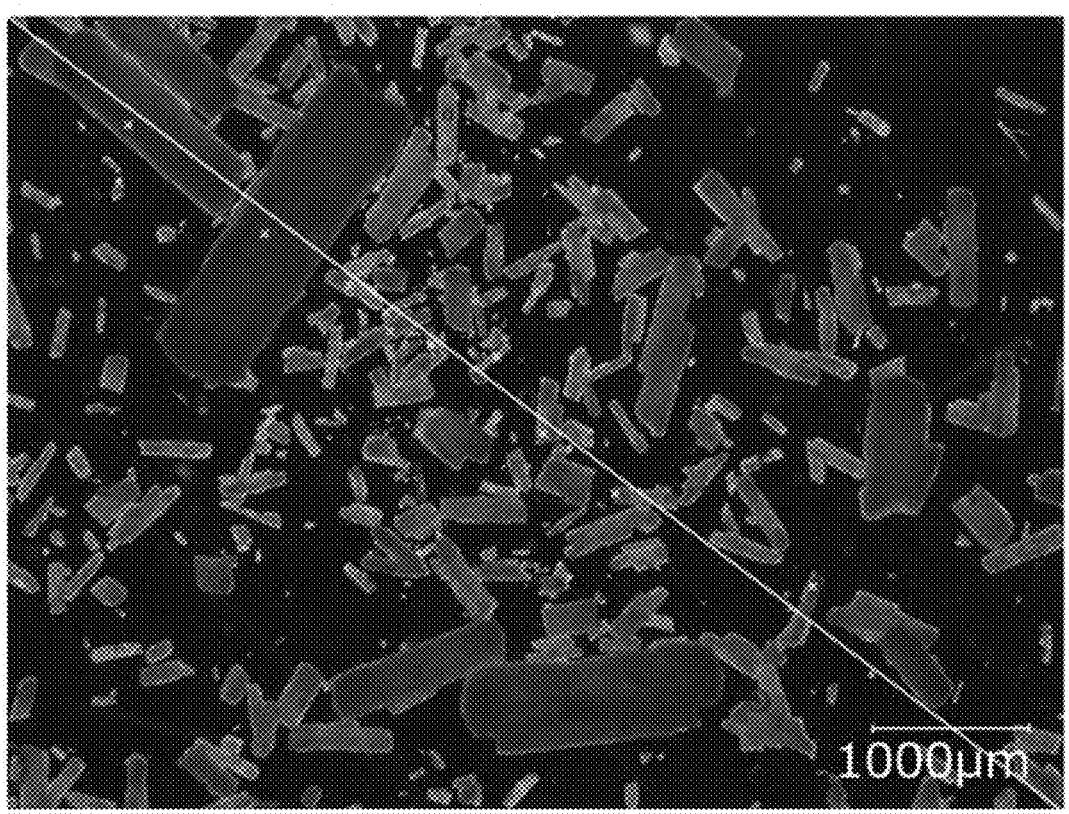

D-ALLOSE CRYSTAL AND PRODUCTION METHOD THEREOF

CROSS REFERENCE TO RELATED APPLICATIONS

This Application is Divisional of U.S. application Ser. No. 17/116,039 filed Dec. 9, 2020, which claims priority from Japanese Patent Application No. 2019-222673, filed on Dec. 10, 2019 in the Japan Intellectual Property Office, the disclosures of which are incorporated herein by reference in their entireties.

BACKGROUND OF THE INVENTION

Field of the Invention

The present invention relates to a high-purity D-allose crystal and a method for producing the crystal.

Description of the Related Art

D-allose is a hexose aldose and is a "rare sugar" having a sweetness of about 80% of sugar. Among rare sugars, D-allose is a monosaccharide having physiological functions that has been well-studied second only to D-psicose. It has been found that D-allose has an effect for suppressing an increase in blood pressure, an effect for suppressing generation of active oxygen in cells, and an effect for suppressing growth of cancer cells.

D-allose is obtained by isomerizing D-psicose with an enzyme or the like in many cases, so that a D-allose crystal is produced from a D-allose solution containing not a small amount of D-psicose as a starting material.

In the case of using a D-allose solution containing D-psicose as a starting material, a method of crystallizing D-psicose and D-allose as a complex (Japanese Patent Laid-Open No. 2011-205913) and a method of crystallizing D-allose only by using a difference in solubility in ethanol (Japanese Patent Laid-Open No. 2004-298106) have been known so far. By these methods, however, high-purity D-allose crystals cannot be efficiently obtained. It has been therefore desired to develop a method capable of efficiently obtaining high-purity D-allose crystals without use of an organic solvent such as ethanol.

It is an object of the present invention to provide high-purity D-allose crystals and a method of efficiently obtaining the crystals.

SUMMARY OF THE INVENTION

In studying to solve the above problems, the present inventors have found that D-allose crystals include hydrous crystals and anhydrous crystals. As a result of initial studying of a method of crystallizing an anhydride having high storage stability in a D-allose solution, it has been found that the anhydrous crystals have a very poor yield due to the fine needle-shape, while the hydrous crystals have a high yield due to a larger particle size. Accordingly, a method including crystallizing a hydrous substance in a D-allose solution to obtain "hydrous D-allose crystals", and then removing the crystallization water thereof to obtain "anhydrous D-allose crystals" has been studied in detail.

As a result, the inventors have obtained an efficient "method for producing D-allose crystals" and novel high-purity "anhydrous D-allose crystals" having a large particle size and good fluidity. Specifically, it has been found that novel "anhydrous D-allose crystals" can be obtained by adding D-allose seed crystals to a D-allose-containing solution having a purity of D-allose of at least 80% (g/g) in a solute, in a metastable region in a supersaturated state of 30° C. or less, then lowering the temperature of the solution by 10° C. or more for cooling and crystallization to initially obtain "hydrous D-allose crystals", and removing the crystallization water thereof in a specified temperature zone.

In other words, the present invention has been completed based on the findings described above, and is composed of the following (1) to (9).

{1} The first invention relates to the following "method for producing a hydrous D-allose crystal".

(1) A method for producing a hydrous D-allose crystal by adding a D-allose seed crystal to a D-allose-containing solution, comprising steps of: providing a D-allose-containing solution having a purity of D-allose of at least 80% (g/g) in a solute, adjusting the D-allose-containing solution to that in a metastable region in the supersaturated solution at 30° C. or less, adding a D-allose seed crystal to said D-allose-containing solution and then cooling the D-allose-containing solution by lowering the temperature of the solution at least by 10° C. or more for crystallization of the hydrous D-allose crystal.

(2) The method for producing a hydrous D-allose crystal according to (1), wherein the metastable region of the D-allose-containing solution to which the D-allose seed crystal is added has a degree of supersaturation of 1.02 to 1.30.

(3) The method for producing a hydrous D-allose crystal according to (1) or (2), wherein the metastable region of the D-allose-containing solution to which the D-allose seed crystal is added has a relationship between Brix of the D-allose-containing solution and temperature (° C.) satisfying: 1.03×Temperature+23.10≤Brix≤0.94×Temperature+34.90.

(4) The method for producing a hydrous D-allose crystal according to any one of (1) to (3), wherein the amount of the added D-allose seed crystal is in an amount of 1.0 to 3.0 mass % based on D-allose in the D-allose-containing solution.

(5) The method for producing a hydrous D-allose crystal according to (4), wherein the method has a yield of the hydrous D-allose crystal from the D-allose-containing solution of 53% or more.

{2} The second invention relates to the following "method for producing an anhydrous D-allose crystal".

(6) A method for producing an anhydrous D-allose crystal, comprising steps of:

preparing the hydrous D-allose crystal by the production method according to any one of (1) to (5), and drying the hydrous D-allose crystal at 30 to 65° C.

(7) The method for producing an anhydrous D-allose crystal according to (6, wherein the anhydrous D-allose crystal satisfies the following (A) and (B):

(A) a purity of 99% or more (B) a repose angle of less than 46 degrees.

(8) The method for producing an anhydrous D-allose crystal according to (7), wherein the anhydrous D-allose crystal further satisfies the following (C):

(C) an aspect ratio of a particle of 1.0 to 10.

(9) The method for producing an anhydrous D-allose crystal according to (7) or (8), wherein the anhydrous D-allose crystal further satisfies the following (D):
(D) an average particle size of 200 to 800 μm.

{3} The third invention relates to the following "anhydrous D-allose crystal".

(10) An anhydrous D-allose crystal satisfying the following (A) and (B):
(A) a purity of 99% or more
(B) a repose angle of less than 46 degrees.
(11) The anhydrous D-allose crystal according to (10), further satisfying the following (C):
(C) an aspect ratio of a particle of 1.0 to 10.
(12) The anhydrous D-allose crystal according to (10) or (11), further satisfying the following (D):
(D) an average particle size of 200 to 800 μm.

Advantageous Effect of Invention

The "anhydrous D-allose crystals" of the present invention have not only an extremely high purity of 99.0% (g/g) or more but also excellent fluidity due to the particles not having a fine needle shape. Also, by the "method for producing anhydrous D-allose crystals" of the present invention, high-purity anhydrous D-allose crystals can be produced at a high yield. Accordingly, the "anhydrous D-allose crystals" and the "method for producing anhydrous D-allose crystals" of the present invention are able to provide raw material products with high marketability suitable for various uses such as foods, functional foods, dietary supplements, pharmaceuticals and cosmetics.

BRIEF DESCRIPTION OF THE DRAWINGS

FIG. 1 shows a solubility curve (solid line at the left end) and a supersolubility curve (solid line at the right end) of D-allose together with a range of conditions suitable for obtaining hydrous D-allose crystals of the present invention (upper limit and lower limit; between a dashed line located second from the left and a dashed line located third from the left);

FIG. 2 shows the particle size distribution of anhydrous D-allose crystals (Test No. 1); and FIG. 3 is a microscopic picture of anhydrous D-allose crystals (Test No. 1).

DETAILED DESCRIPTION OF THE PREFERRED EMBODIMENT

The term "supersaturated state" in the present invention refers to an unstable state in which a solute is dissolved in excess of the dissolution ability of a solvent, and a state in which the solute can be crystallized as a solid. The "degree of supersaturation" is a relative concentration to a saturation concentration of 1. For example, a concentration at 10% (g/g) higher than the saturation concentration is represented by "1.10".

The saturation concentration usually expressed in terms of solid content % (g/g) cannot be immediately measured in the case of observing the change with time, so that the concentration control becomes difficult. In the present invention, therefore, a saturated solution % (g/g) on a known solubility curve of D-allose at each temperature (for example, "Aqueous Phase Behavior of the Rare Monosaccharides D-Allose and X-ray Crystallographic Analysis of D-allose Dihydrate", Bull. Chem. Soc. Jpn. 2015, 88, 465-470, Table S1 in Supporting Information) has been prepared to measure Brix, and a solubility curve of D-allose showing the relationship between Brix and temperature (C) (a solid line at the left end of the graph of FIG. 1) has been made to derive a relational expression between solid content % (g/g) and Brix (the following [Expression 1]). In the following, the solid content % (g/g) of a solution is replaced with the Brix value. The solid content value may be calculated backward by using the following expression, and the degree of supersaturation described above may be obtained from the Brix value.

$$\text{Solid content \% (g/g)} = (1.0134 \times \text{Brix}) - 0.2341 \quad \text{[Expression 1]}$$

The term "metastable region" in a supersaturated state of the present invention refers to a range of the concentration of a solution from the saturation concentration to the lowest supersaturation concentration at which a solute precipitates (hereinafter referred to as "supersolubility", and in the case of D-allose, shown by the solid line at the right end in the graph in FIG. 1). Within the range, no spontaneous formation of crystal nucleus occurs, but when crystals are put in from the outside, the crystals grow spontaneously and become large. However, when the solution is rapidly cooled or excessively concentrated, deviation from the metastable region easily occurs to cause crystal nucleation instead of crystal growth, so that a plurality of fine crystals are formed. Accordingly, in order to obtain crystals having an appropriate size, it is necessary to perform crystallization at an appropriate rate while maintaining the solution in the "metastable region". Since the "metastable region" differs depending on the solute or depending whether the solute is an anhydride or a hydrous substance, it is necessary to examine each solute in detail while considering the effects of external conditions, impurities, temperature, concentration, etc. Being in the "metastable region" is only a necessary condition for crystallization and is not a sufficient condition, it is therefore necessary to further study the conditions for crystallization suitable for the solute in detail.

As a method for obtaining the hydrous D-allose crystals of the present invention, it is essential to add D-allose seed crystals in the "metastable region in a supersaturated state", and the range in terms of the degree of supersaturation needs to be from 1.02 to 1.30, with a Brix in the range satisfying the following Expression 2.

$$1.03 \times \text{Temperature} + 23.10 \leq \text{Brix} \leq 0.94 \times \text{Temperature} + 34.90 \quad \text{[Expression 2]}$$

As a method for obtaining the hydrous D-allose crystal of the present invention, it is essential to add D-allose seed crystals to the "metastable region in a supersaturated state" described above. In the range, addition of the D-allose seed crystals in the temperature range of 30° C. or less allows to obtain hydrous D-allose crystals having a larger particle size with high fluidity. Also, cooling and crystallization performed at a temperature lowered at least by 5° C. or more, preferably 8° C. or more, more preferably 10° C. or more, from the temperature for addition of the D-allose seed crystals enables to obtain hydrous D-allose crystals having further higher fluidity.

The term "hydrous D-allose crystals" in the present invention does not refer to anhydrous D-allose crystals simply containing absorbed water, but refer to D-allose crystals with crystallization water. Usually, in order to efficiently obtain crystals, the purity of the solute in the solution is preferably close to 100%. In contrast, in the method of obtaining hydrous D-allose crystals of the present invention, the purity of D-allose in the solute in the solution may be at least 80% (g/g), preferably 85% (g/g) or more, more preferably 90% (g/g) or more, to obtain hydrous D-allose crystals having a purity of 99.0% or more.

Although the "D-allose seed crystals" used for obtaining the hydrous D-allose crystals of the present invention may be hydrous or anhydrous, preferably anhydrous in consideration of variation of the concentration of the D-allose solution due to the crystallization water. The purity thereof is not particularly limited, and from the viewpoint of workability of crystallization, being preferably 80% (g/g) or more, more preferably 90% (g/g) or more, 95% (g/g) or more, 99% (g/g) or more. Also, the shape of the seed crystals is not particularly limited, and in order to obtain a crystal product having better fluidity, the average particle size is preferably 90 μm or more (166-mesh on, standard sieve in accordance with JIS Z 8801, the rest is omitted), and more preferably 180 μm or more (83-mesh on). For crystallization, it is necessary to add at least 0.5 mass % or more, or 1.0 mass % or more, of D-allose seed crystals to the D-allose in a D-allose-containing solution, and in order to obtain a crystal substance having excellent fluidity, addition may be performed in the range of 0.5 to 5.0 mass %, more preferably 0.7 to 4.0 mass %, still more preferably 1.0 to 3.0 mass %.

According to the method of the present invention, the "yield" of the hydrous D-allose crystals obtained from a D-allose-containing solution (value calculated as the percentage of the mass of solid D-allose collected as crystal relative to the mass of D-allose in the raw material D-allose-containing solution (recovery percentage of the solid D-allose), based on the later explained Expression 3) is at least 53%, and may be at least 60%, at least 65%, or at least 70% in some cases. Accordingly, it can be deemed that the method for producing hydrous D-allose crystals of the present invention is a production method with a very high yield.

The "anhydrous D-allose crystals" in the present invention refer to not only "anhydrous D-allose crystals" precipitated in a D-allose-containing solution but also one obtained by precipitating hydrous D-allose crystals in a D-allose-containing solution and then removing crystallization water. When anhydrous D-allose crystals are obtained by obtaining hydrous D-allose crystals in a D-allose-containing solution and then drying the hydrous D-allose crystals to remove crystallization water, the drying temperature may be at least 30° C. or more and 65° C. or less. From the viewpoint of preventing the D-allose crystals from being consolidated to each other, the upper limit is preferably 60° C. or less, more preferably 55° C. or less, still more preferably 50° C. or less.

The "anhydrous D-allose crystals" of the present invention with a purity of 99% or more have a melting point (Tm) in differential scanning calorimetry (DSC) of 145° C.±5° C. and a melting enthalpy (ΔH) of 200 to 250 J/g, which are close to the values exhibited by known anhydrous D-allose crystals. On the other hand, the "anhydrous D-allose crystals" of the present invention have a repose angle of less than 46 degrees, which is smaller than those of known anhydrous D-allose crystals, being extremely excellent in fluidity. Also, the "anhydrous D-allose crystals" of the present invention have a granular shape instead of a fine needle shape, with an average particle size of 200 to 800 μm, 250 to 700 μm, or 300 to 600 μm.

The melting point (Tm) in the DSC refers to the melting start temperature of the endothermic peak obtained by DSC measurement (temperature at the extrapolated intersection of the base line and the maximum slope line of the endothermic peak), and the melting enthalpy (ΔH) refers to the area of the endothermic peak (ASTM D3418-15, Standard Test Method for Transition Temperatures and Enthalpies of Fusion and Crystallization of Polymers by Differential Scanning calorimetry). Further, in the present invention, the average particle size refers to the volume-based average particle size d[4,3], which is usually measured with a laser diffraction particle size distribution analyzer.

The "anhydrous D-allose crystals" of the present invention have an extremely large average particle size as described above and are not in a fine needle form, having a characteristic aspect ratio of the crystal. In the present invention, the aspect ratio refers to the ratio of the long diameter to the short diameter of a crystal (short diameter: minimum length of lines passing through the center of gravity of the plane shape of a crystal, long diameter: maximum length of a crystal measured orthogonal to the short diameter). In the present specification, the aspect ratio in a numerical range from A to B (A and B: arbitrary numbers) means that all of the aspect ratios of a specified number (preferably at least 10, for example 10) of crystal particles randomly selected are within the numerical range. Example of random selection of crystal particles includes a method comprising taking a microscopic picture of crystals at 20× to 50× magnification and, from the crystals on the diagonal line drawn from the upper left to the lower right of the microscopic picture taken, selecting 10 crystals with a full body shown in order from the upper left on the diagonal line. Specifically, the aspect ratio is preferably 1.0 to 10.0, more preferably 2.0 to 8.0, still more preferably 2.0 to 7.0.

The anhydrous D-allose crystals of the present invention are not in a fine needle form, and unconventionally have a relatively large particle size with high fluidity, so that raw material products with high marketability suitable for various uses such as foods, functional foods, dietary supplements, pharmaceuticals and cosmetics can be provided therefrom.

EXAMPLES

Examples are shown as follows to illustrate the present invention, though the present invention is not limited thereto.

(1) Studying Relationship Between Brix and Temperature for Crystallization of D-Allose In the following experiments, in order to smoothly control the numerical values of the solid content, it was decided to derive the relational expression between the solid content % (g/g) of D-allose and Brix. First, a saturated solution % (g/g) at each temperature on a known solubility curve of D-allose was prepared to measure Brix, and the relationship between the Brix and the temperature (° C.) was shown as a solubility curve of D-allose (solid line in the graph at the upper end in FIG. 1). The relational expression between the solid content % (g/g) and Brix is as shown in [Expression 1] described above.

The "metastable region" in a supersaturated state of D-allose refers to the range of the concentration of the solution from the saturated concentration to the minimum supersaturated concentration at which a solute precipitates, and the supersolubility of D-allose can be obtained by measuring Brix when crystals spontaneously precipitate without addition of seed crystals at each temperature. The relationship between the Brix and the temperature (° C.) is shown as a supersolubility curve of D-allose (solid line in the graph at the lower end in FIG. 1).

Next, a D-allose solution at each degree of supersaturation was prepared as follows. First, D-allose crystals having a purity of 99% were dissolved in pure water and appropriately concentrated by a rotary evaporator (50° C., 15 to 30 hPa (abs)) to obtain a supersaturated solution having a desired concentration. Each thereof was cooled to any one temperature of 15, 20, 25 and 30° C. To the supersaturated solution of D-allose at each temperature and each degree of supersaturation thus prepared, a dry powder of hydrous D-allose having a purity of 99% (particle size: passed through a 42-mesh sieve and remained on an 83-mesh sieve) was added in an amount of 1.0% (g/g) based on D-allose (g) in the supersaturated solution, and then the mixture was shaken for 18 hours in a thermostat chamber equipped with a shaker. After subsequent centrifugation (12000 rpm (centrifugal acceleration 13000 G), 10 minutes), the Brix of the supernatant was measured.

When the difference in Brix between at the time of start of shaking and at the time of end of shaking was 1.0 or more, it was determined that crystallization had progressed. Further, when a white turbidity was visually observed, it was determined that the temperature and the degree of supersaturation were suitable as conditions for crystallization. When the white turbidity was completely solidified as a whole into an uncrushable state, it was determined that the conditions were not suitable for crystallization due to unavailability for use.

The results are shown in Table 1. From the results, the relationship between Brix and temperature determined to be suitable for crystallization (rated as good in the comprehensive evaluation in Table 1) was plotted on a graph to obtain the upper limit and the lower limit, which are shown as dashed lines in the graph in FIG. 1.

TABLE 1

| Temp. | Degree of super-saturation | Brix (%) before shaking | Brix (%) after shaking | Appearance | Comprehensive evaluation |
|---|---|---|---|---|---|
| 15° C. | 1.01 | 35.5 | 35.7 | | |
| | 1.02 | 35.9 | 36.0 | | |
| | 1.03 | 36.2 | 36.1 | | |
| | 1.04 | 36.6 | 36.2 | | |
| | 1.05 | 37.0 | 37.2 | | |
| | 1.10 | 38.6 | 35.0 | | Good |
| | 1.15 | 40.5 | 34.9 | | Good |
| | 1.20 | 42.2 | 35.0 | | Good |
| | 1.25 | 44.0 | 35.0 | | Good |
| | 1.30 | 45.8 | 35.0 | | Good |
| | 1.40 | 49.2 | Unmeasurable | Consolidated | |
| 20° C. | 1.05 | 42.9 | 43.4 | | |
| | 1.15 | 46.9 | 40.7 | | Good |
| | 1.21 | 49.3 | 40.4 | | Good |
| | 1.25 | 51.2 | 40.6 | | Good |
| | 1.30 | 53.0 | 41.2 | | Good |
| | 1.36 | 55.6 | Unmeasurable | Consolidated | |
| | 1.39 | 57.0 | Unmeasurable | Consolidated | |
| 25° C. | 1.01 | 47.3 | 47.4 | | |
| | 1.02 | 47.8 | 48.0 | | |
| | 1.03 | 48.2 | 48.2 | | |
| | 1.04 | 48.6 | 48.6 | | |
| | 1.05 | 49.2 | 46.3 | | Good |
| | 1.10 | 51.4 | 46.1 | | Good |
| | 1.15 | 53.7 | 46.3 | | Good |
| | 1.20 | 56.1 | 46.8 | | Good |
| | 1.25 | 58.4 | 46.9 | | Good |
| | 1.30 | 60.7 | Unmeasurable | Consolidated | |
| | 1.35 | 63.0 | Unmeasurable | Consolidated | |
| | 1.40 | 65.6 | Unmeasurable | Consolidated | |
| 30° C. | 1.01 | 53.4 | 53.2 | | |
| | 1.02 | 54.0 | 52.4 | | Good |
| | 1.03 | 54.6 | 52.4 | | Good |
| | 1.04 | 55.0 | 52.4 | | Good |
| | 1.05 | 55.6 | 52.3 | | Good |
| | 1.10 | 58.3 | 52.2 | | Good |
| | 1.15 | 61.0 | 52.0 | | Good |
| | 1.20 | 63.6 | Unmeasurable | Consolidated | |

(2) Studying Amount of Seed Crystals Added and Particle Size Thereof

Next, the amount of seed crystals added and the particle size suitable for crystallization were studied. A supersaturated solution of D-allose having a Brix of 49.1 (20° C.) was prepared, and the same procedure as in the previous experiment was performed except for the size and the amount added of the seed crystals. The seed crystals used were a hydrous D-allose having a purity of 99% or more, with a particle size that "passed through a 42-mesh sieve and remained on a 83-mesh sieve" (42 mesh pass/83 mesh on) or "passed through a 120-mesh sieve and remained on a 166-mesh sieve" (120-mesh pass/166-mesh on). The amount added thereof was controlled to 0.1, 0.5, 1.0 or 3.0 mass % based on D-allose in the D-allose solution.

The results are shown in Table 2.

TABLE 2

| | 42-mesh pass/83-mesh on | | 120-mesh pass/166-mesh on | |
|---|---|---|---|---|
| Seed crystal (%) | Brix | Presence or absence of crystal | Brix | Presence or absence of crystal |
| 0.1 | 50.0 | Absent | 49.4 | Absent |
| 0.5 | 41.1 | Present | 49.0 | Absent |
| 1.0 | 41.4 | Present | 41.4 | Present |
| 3.0 | 41.0 | Present | 41.0 | Present |

As a result, regarding the solution in which crystals were not visually observed, the Brix in the supernatant after shaking for 18 hours hardly decreased. The crystallized product obtained was hydrous D-allose crystals, and the anhydrous D-allose crystals obtained by drying the crystallized product at 40° C. had a large particle size, with a shape different from a fine needle. Although it is known that use of seed crystals having a too small particle size produce a fine needle-like crystal substance, it was just found that when a hydrous D-allose crystals obtained are made into anhydrous D-allose crystals, with seed crystals in an amount added of 1.0% or more, a crystal product having a large particle size can be obtained without serious consideration of the size of the seed crystal.

(3) Studying Conditions for Crystallization

Next, the effects of the purity of D-allose in the raw material solution and the change in cooling rate for crystallization on the purity, yield and fluidity of the anhydrous D-allose crystal finally obtained were studied.

A D-allose solution having each purity prepared from hydrous D-allose crystals having a purity of 99% or more and D-psicose crystals having a purity of 99% or more was concentrated by a rotary evaporator (50° C., 15 to 30 hPa) to obtain a concentrated solution, which was then subjected to a crystallization process. Specifically, first, a beaker containing the concentrated solution was set in a crystallization apparatus capable of controlling temperature, and the temperature was controlled to crystallization start temperature while stirring at 100 rpm. Seed crystals (dry powder of hydrous D-allose, 42-mesh pass/83-mesh on) were added thereto in an amount of 1 mass % or 3 mass % based on D-allose in the solution of D-allose, and program cooling was started at a stirring rate of 90 rpm. Each of the conditions for crystallization on this occasion is shown in Table 3.

TABLE 3

| Test No. | Purity (%) of raw material | Brix (%) at start of crystallization | Start Temp. *1 (° C.) | End Temp. *2 (° C.) | Δ Temp.*3 (° C.) | Cooling rate (° C./h) | Retention time (h) | Amount of seed crystal added (mass %) |
|---|---|---|---|---|---|---|---|---|
| 1 | 99.4 | 56 | 25 | 10 | 15 | 3.75 | 0 | 1 |
| 2 | 99.4 | 56 | 25 | 10 | 15 | 3.75 | 0 | 3 |
| 3 | 94.5 | 56 | 25 | 10 | 15 | 3.75 | 0 | 1 |
| 4 | 90.2 | 56 | 25 | 10 | 15 | 3.75 | 0 | 1 |
| 5 | 80.3 | 56 | 25 | 10 | 15 | 3.75 | 0 | 1 |
| 6 | 70.7 | 56 | 25 | 10 | 15 | 3.75 | 0 | 1 |
| 7 | 99.4 | 54 | 25 | 10 | 15 | 3.75 | 0 | 1 |
| 8 | 99.4 | 60.6 | 30 | 20 | 10 | 3.75 | 1 | 1 |
| 9 | 99.4 | 58 | 25 | 15 | 10 | 3.75 | 1 | 1 |
| 10 | 99.6 | 51 | 20 | 10 | 10 | 3.75 | 1 | 1 |
| 11 | 99.7 | 45.7 | 15 | 5 | 10 | 3.75 | 1 | 1 |
| 12 | 99.4 | 60.6 | 30 | 5 | 25 | 25 | 1 | 1 |

*1 crystallization start temperature
*2 cooling end temperature
*3 difference between crystallization start temperature and cooling end temperature After end of cooling, 40 to 50 g of each massecuite was collected in two stainless steel separation centrifuge tubes equipped with milk filter paper (manufactured by ADVANTEC, No. 1026-B), and hydrous crystals obtained by removing supernatant (mother liquor) through centrifugation at 2000 rpm (920 G) for 60 minutes were dried by a rotary evaporator (30° C., 20 hPa (abs), about 2 hours) to obtain anhydrous crystals. Next, the anhydrous crystal made into a solution with a Brix of 5 was desalted and filtered to be subjected to HPLC analysis (column: CK08EC, temperature: 80° C., dissolution liquid: pure water, flow rate: 0.4 ml/min, detector: RI, analysis time: 90 minutes). The purity of solid D-allose was determined by the area percentage method.

"Percentage of mass of solid D-allose collected as crystals relative to mass of D-allose in raw material D-allose-containing solution (recovery percentage of solid D-allose) (Yield) was calculated by the following Expression 3.

Yield (%)={(A−B)/A}×100     [Expression 3]

In the expression, A represents: Weight of massecuite collected (g)×Solid content of raw material solution (% (g/g)×Purity of D-allose in raw material solution, and B represents: Weight of mother liquor collected (g)×Solid content of mother liquor (% (g/g))×Purity of D-allose in mother liquor (% (g/g)). The conversion from Brix to solid content is performed using [Expression 1].

The fluidity of the anhydrous D-allose crystals obtained by drying the hydrous crystals obtained in each of Tests Nos. 1 to 12 with an evaporator (30° C., 20 hPa (abs), about 2 hours) as described above was evaluated by the repose angle measured by a powder tester PT-E (manufactured by Hosokawa Micron Corporation). Specifically, a sample was dropped and deposited on a disk, and the inclination angle was measured from three directions to obtain an average value. From the average value, the degree of fluidity was evaluated according to Table 1 in the Japanese Pharmacopoeia, 17th edition, Reference Information G2 physical property-related "Powder Fluidity" (same as the so-called Carr's fluidity index table, shown as Table 4). The results are shown in Table 5.

TABLE 4

| Degree of fluidity | Measure for preventing cross-linking | Repose angle (°) |
|---|---|---|
| Extremely good | | 25~30 |
| Good | | 31~35 |
| Somewhat good | Unnecessary | 36~40 |
| Passable | Presence of cross-linking at limiting point | 41~45 |
| Somewhat poor | In need of stirring or shaking | 46~55 |
| Poor | | 56~65 |
| Extremely poor | | >66 |

TABLE 5

| Test No. | Purity (%) of crystal | Yield (%) | Repose angle (degrees) | Degree of fluidity |
|---|---|---|---|---|
| 1 | 99.9 | 63.9 | 43.0 | Passable |
| 2 | 99.9 | 66.0 | 42.7 | Passable |
| 3 | 99.7 | 64.8 | 42.0 | Passable |
| 4 | 99.6 | 61.7 | 42.3 | Passable |
| 5 | 99.4 | 53.8 | 45.7 | Passable |
| 6 | 99.0 | 45.9 | — | — |
| 7 | 99.4 | 58.2 | 41.0 | Passable |
| 8 | 99.9 | 63.0 | 41.7 | Passable |
| 9 | 99.9 | 66.3 | 41.0 | Passable |
| 10 | 99.9 | 58.5 | 41.3 | Passable |
| 11 | 99.9 | — | — | — |
| 12 | 99.9 | 70.2 | 41.3 | Passable |

As a result, it has been found that with a purity of D-allose as solid content in the raw material solution of 99.4 to 80.3%, and an amount of the seed crystals added of 1 mass % or 3 mass % as in the previous experimental results, anhydrous D-allose crystals having a purity of D-allose of 99% or more and a "passable" degree of fluidity can be obtained. In contrast, with a purity of Dallose as solid content of 70.7%, although it was possible to obtain hydrous D-allose crystals, the total amount of the crystals adhered to the wall surface of a container in the drying step, so that anhydrous D-allose crystals were unable to be collected.

Also, with a degree of supersaturation of the solution of D-allose immediately before addition of seed crystals of 1.02 to 1.30, anhydrous D-allose crystals having a purity of D-allose of 99% or more and a "passable" degree of fluidity were able to be obtained.

Regarding the cooling temperature, it has been found that with cooling from 30° C. to 20° C., 25° C. to 15° C., or 20°

C. to 10° C., anhydrous D-allose crystals having a purity of D-allose of 99% or more and a "passable" degree of fluidity were able to be obtained. In contrast, with cooling from 15° C. to 5° C., the total amount of wet crystals were dissolved in mother liquor during centrifugation, so that it was unable to collect crystals.

(4) Studying Conditions for Drying Hydrous D-Allose Crystals

Next, conditions for drying hydrous D-allose crystals were studied. Specifically, employing ultra-low humidity drying, conductive heat transfer drying, or convection heat transfer drying as a drying method, appropriate conditions of drying temperature and time were studied.

In the ultra-low humidity drying, a fully automatic ultra-low humidity dry box (Mcdry, manufactured by ERC Co., Ltd.) was used. On a stainless steel vat, 250 g of hydrous D-allose crystals having a purity of 99.9% (water content: 17.7%) were spread and left to stand in a dry box at a relative humidity of 5% or less and a temperature of 20 to 24° C. for drying until the decrease in weight stopped.

In the conduction heat transfer drying, an oblique-axis kneader (GNV60/10ST, manufactured by Samson Co., Ltd.) was used. Hydrous D-allose crystals in an amount of 3000 g having a purity of 99.9% (water content: 17.7%) were dried by heat conducted from a heating jacket at a temperature of 40° C., 50° C., 60° C. or 70° C. with stirring under vacuum of 760 mmHg until the decrease in water content stopped (far-infrared moisture meter, 105° C.).

In the convection heat transfer drying, a flow coater (fluidized bed granulator type 5, manufactured by Freund Corporation) was used. To floating and flowing hydrous D-allose crystals in an amount of 2000 g (purity: 99.9%, water content: 17.7%), warm air (40° C. or 50° C.) was supplied for 5 minutes (6000 L/min) for drying until the decrease in water content stopped.

In order to measure the water content in the crystals obtained by each of the drying methods, drying under reduced pressure under conditions at 70° C. for 18 hours was performed to calculate the water content in the crystals from the weight loss through the drying under reduced pressure. The repose angle was measured by the method described above to determine the degree of fluidity. The yield rate was calculated by the following expression.

Yield rate (%)=(D/C)×100  [Expression 4]

In the expression, C represents: Weight of crystals fed into drying apparatus (g)×{(1−(Water content therein (%)/100)}, and D represents: Weight of crystals collected from drying apparatus (g)×{(1−(Water content therein (%)/100)}.

The results of the drying tests are shown in Table 6.

TABLE 6

| Conditions for drying | Water content (%) after drying | Repose angle (degrees) | Degree of fluidity | Yield rate (%) |
|---|---|---|---|---|
| Ultra-low humidity drying (20 to 24° C.) | 0.052 | 45.7 | Passable | 88.7 |
| Conductive heat transfer drying at 40° C. | 0.13 | 41.3 | Passable | 96.3 |
| Conductive heat transfer drying at 50° C. | 0.099 | 42 | Passable | 97.6 |
| Conductive heat transfer drying at 60° C. | 0.18 | 41.7 | Passable | 85.4 |
| Conductive heat transfer drying at 70° C. | 0.105 | 44 | Passable | 41.0 |
| Convection heat transfer drying at 50° C., Air supply: 4700 L/min | 0.13 | 42 | Passable | 87.4 |
| Convection heat transfer drying at 40° C., Air supply: 3900 L/min | 0.14 | 41.3 | Passable | 93.4 |
| Convection heat transfer drying at 40° C., Air supply: 6000 L/min | 0.13 | 41.7 | Passable | 94.7 |

It has been found that by any of the methods (apparatuses) for drying hydrous D-allose crystals, anhydrous D-allose crystals having a "passable" degree of fluidity can be obtained at a good yield rate. It has been also found that with a drying temperature of 40 to 60° C., anhydrous D-allose crystals having a "passable" degree of fluidity can be obtained. However, in the ultra-low humidity drying (20 to 24° C.), conductive heat transfer drying at 60° C., and convection heat transfer drying at 50° C., a part of the crystals adhered to the wall surface of a container, so that the yield rate slightly decreased. Also, in conductive heat transfer drying at 70° C., the crystals adhered to the wall surface of the container, so that the yield rate drastically decreased. In the case of focusing on yield rate, it is therefore preferable that the hydrous D-allose crystals be dried in the range of 40 to 50° C., while being stirred or fluidized.

All of the XRD diffraction profiles of the crystals obtained by drying hydrous D-allose crystals (Test Nos. 1 to 5, 7 to 10, and 12) were confirmed to have a similar diffraction profile and to be similar to the diffraction profile of known anhydrous D-allose crystals, so that the crystals were considered to have a same crystal lattice structure.

(5) Particle Size Distribution and Aspect Ratio of Anhydrous D-Allose Crystals

Next, the particle size distribution of the anhydrous D-allose crystals of the present invention was examined. Specifically, the anhydrous D-allose crystals obtained in the previous Test Nos. 1 to 5, 7 to 10 and 12, were subjected to measurement of particle size distribution under the measurement conditions shown in Table 7 using "Mastersizer 3000" and a "dry dispersion unit Aero S" manufactured by Malvern Instruments. More specifically, the measurement was repeated 5 times, and the average value of the 5 times measurements was used. No great variability was seen among the 5 times measurement values. The particle size distribution was expressed on a volume basis, and the volume-based average particle size d[4,3] and standard deviation σ were recorded. Also, the coefficient of variation CV=σ/d[4,3] was calculated in order to relatively evaluate the variation in the particle size distribution.

TABLE 7

| | |
|---|---|
| Dispersion pressure of sample | 1.0 bar (gauge) |
| Light source | He-Ne Laser (wavelength: 632.8 nm) |
| Intensity of scattered light | 0.1~20% |
| Analysis conditions | Mie scattering/non-spherical/general purpose mode, refractive index: 1.538 + 0.01 i (using "Sugar" of database attached to apparatus) |

The volume-based average particle size d[4,3], standard deviation σ, and coefficient of variation CV of each sample are shown in Table 8. The particle size distribution of the D-allose crystals obtained in Test No. 1 is shown in FIG. 2. In the measurement using a laser diffraction particle size distribution analyzer, the average particle size was 333 to 708 μm, and the coefficient of variation was 0.47 to 0.76.

TABLE 8

| Test No. | d [4, 3] (μm) | σ (μm) | CV |
|---|---|---|---|
| 1 | 472 | 340 | 0.72 |
| 2 | 563 | 326 | 0.58 |
| 3 | 450 | 255 | 0.57 |
| 4 | 588 | 298 | 0.51 |
| 5 | 498 | 234 | 0.47 |
| 7 | 549 | 309 | 0.56 |
| 8 | 708 | 397 | 0.56 |
| 9 | 600 | 453 | 0.76 |
| 10 | 492 | 322 | 0.65 |
| 12 | 333 | 235 | 0.71 |

Next, the aspect ratio of the anhydrous D-allose crystals of the present invention was examined. Specifically, a microscopic picture of each of the anhydrous D-allose crystals obtained in the previous Test Nos. 1 to 5, 7 to 10 and 12 were taken using "Digital microscope VHX-5000" manufactured by KEYENCE Corporation (50×magnification). Among the crystals on the diagonal line drawn from the upper left to the lower right of the microscopic picture taken, 10 crystals with a full picture shown were selected in order from the upper left and then the long diameter and the short diameter of each crystal were measured for calculation of the aspect ratio (Long diameter/Short diameter, wherein short diameter refers to minimum length of lines passing through the center of gravity of the plane shape of a crystal, and long diameter refers to maximum length of a crystal measured orthogonal to the short diameter). The minimum value of the aspect ratio was 1.1 and the maximum value was 9.6 (Table 9).

TABLE 9

| Sample No. | Aspect ratio | | | | | | | | | |
|---|---|---|---|---|---|---|---|---|---|---|
| | ① | ② | ③ | ④ | ⑤ | ⑥ | ⑦ | ⑧ | ⑨ | ⑩ |
| 1 | 3.5 | 3.4 | 4.1 | 4.4 | 4.5 | 2.2 | 4.3 | 3.6 | 3.5 | 4.1 |
| 2 | 2.9 | 3.0 | 3.5 | 3.5 | 3.0 | 5.5 | 2.6 | 4.9 | 3.0 | 4.1 |
| 3 | 2.5 | 5.4 | 3.9 | 6.2 | 4.5 | 4.3 | 3.0 | 4.7 | 6.1 | 1.5 |
| 4 | 4.3 | 4.0 | 4.2 | 2.0 | 6.0 | 1.1 | 3.9 | 8.1 | 3.8 | 4.1 |
| 5 | 1.1 | 2.7 | 3.2 | 2.9 | 4.7 | 3.0 | 4.9 | 4.1 | 1.6 | 3.8 |
| 7 | 7.2 | 1.7 | 5.2 | 5.5 | 2.5 | 4.1 | 4.3 | 4.9 | 3.5 | 2.0 |
| 8 | 3.5 | 7.7 | 2.0 | 3.6 | 3.1 | 2.8 | 3.8 | 4.7 | 1.7 | 3.3 |
| 9 | 6.2 | 4.3 | 5.7 | 3.0 | 3.5 | 5.9 | 4.6 | 2.6 | 3.6 | 1.9 |
| 10 | 1.6 | 3.9 | 5.6 | 2.1 | 4.0 | 9.6 | 2.3 | 3.3 | 4.6 | 5.4 |
| 12 | 3.1 | 3.3 | 4.2 | 3.8 | 3.6 | 4.4 | 4.7 | 3.7 | 3.7 | 1.3 |

What is claimed is:

1. An anhydrous D-allose crystal satisfying the (A) to (C):
   (A) a purity of 99% or more;
   (B) a repose angle of 43.0 degrees or less; and
   (C) an aspect ratio of a particle of 1.0 to 10.

2. The anhydrous D-allose crystal according to claim 1, further satisfying the following (D):
   (D) an average particle size of 200 to 800 μm.

3. The anhydrous D-allose crystal according to claim 1, further satisfying that the purity of (A) is 99.4% or more.

4. The anhydrous D-allose crystal according to claim 1, further satisfying that the repose angle of (B) is 42.0 degrees or less.

5. The anhydrous D-allose crystal according to claim 1, further satisfying that the repose angle of (B) is 40 degrees or less.

* * * * *